United States Patent [19]

Fritch et al.

[11] Patent Number: 4,607,622
[45] Date of Patent: Aug. 26, 1986

[54] FIBER OPTIC OCULAR ENDOSCOPE

[75] Inventors: Charles D. Fritch, Rte. 11, Box 239B, Bakersfield, Calif. 93308; John B. McAdams, Santa Monica, Calif.

[73] Assignee: Charles D. Fritch, Bakersfield, Calif.

[21] Appl. No.: 722,839

[22] Filed: Apr. 11, 1985

[51] Int. Cl.⁴ .............................................. A61B 1/06
[52] U.S. Cl. .................................................... 128/6
[58] Field of Search ............................. 128/3, 4, 5, 6, 7

[56] References Cited

U.S. PATENT DOCUMENTS

| | | | |
|---|---|---|---|
| 3,261,350 | 7/1966 | Wallace | 128/6 |
| 3,856,000 | 12/1974 | Chikama | 128/6 |
| 3,880,148 | 4/1975 | Kanehira et al. | 128/6 |
| 3,941,121 | 3/1976 | Olinger et al. | 128/6 |
| 4,061,135 | 12/1977 | Widran et al. | 128/6 |
| 4,211,229 | 7/1980 | Wurster | 128/6 X |
| 4,259,948 | 4/1981 | Urban | 128/6 |
| 4,267,828 | 5/1981 | Matsuo | 128/6 |
| 4,319,563 | 3/1982 | Kubota | 128/6 |
| 4,475,539 | 10/1984 | Konomura | 128/6 |

*Primary Examiner*—William H. Grieb
*Attorney, Agent, or Firm*—Singer & Singer

[57] ABSTRACT

An ocular endoscope having a minimum cross-section and designed primarily for use in treating, diagnosing and investigating problems associated with the eye. The probe associated with the endoscope comprises a first bundle of fiber optics carrying light for illumination, a second coaxial bundle of fiber optics terminating in a lens and adapted to view areas being illuminated completely surrounded by a plastic sheath that is semi-rigid and malleable and capable of assuming and holding a preferred shape. In the preferred embodiment a cross-sectional area is elliptical and the sheath contains a port in the area of maximum curvature, which port is adapted to receive a probe. The probe is preferably malleable and may be hollow for accepting instruments or fiber optics connected to an external source of coherent light in the form of a laser for treating purposes.

15 Claims, 10 Drawing Figures

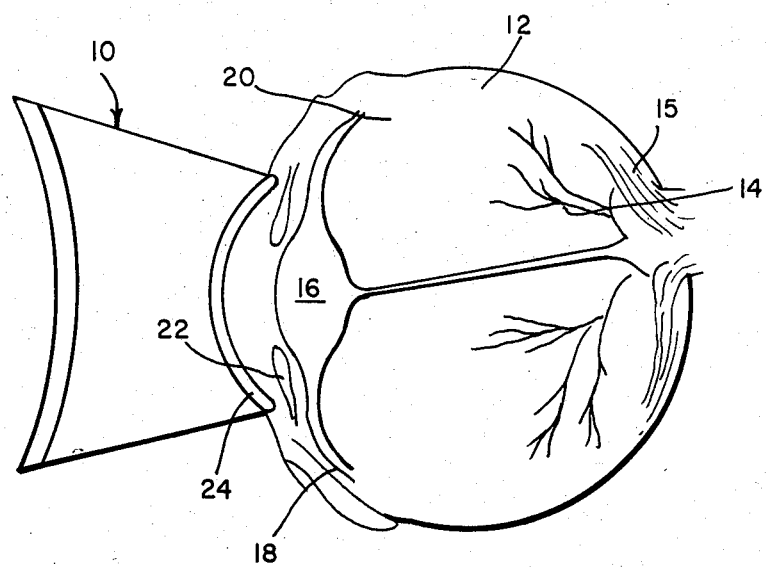
Fig. 1.
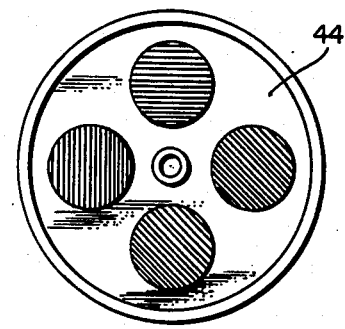
Fig. 3.
Fig. 10.
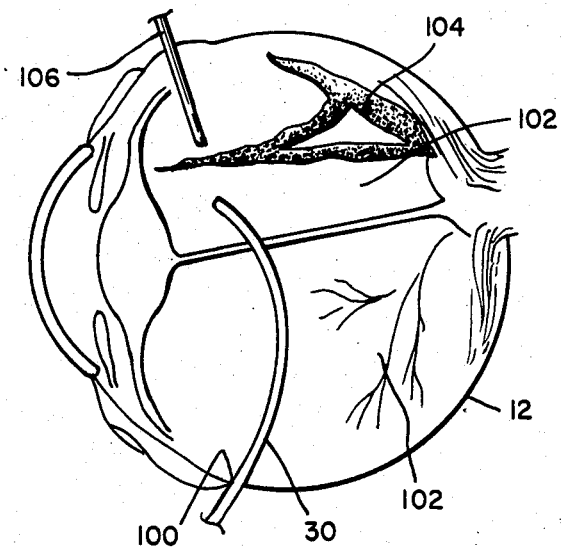
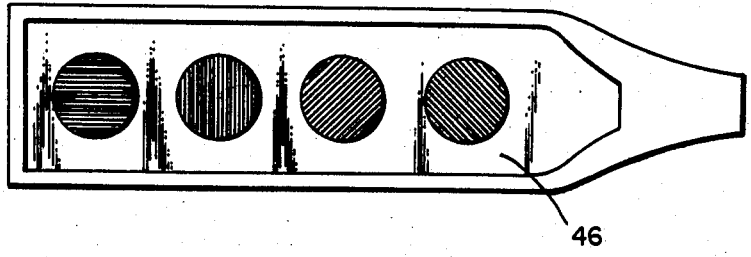
Fig. 4.

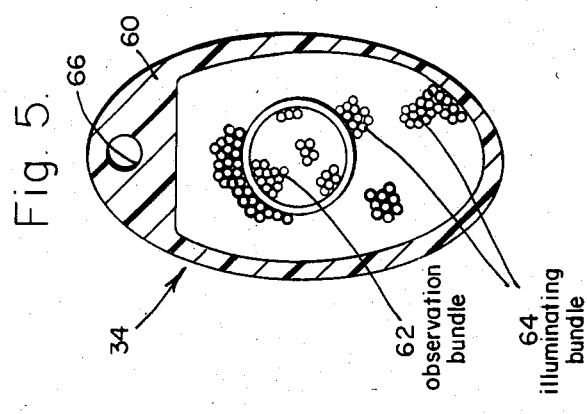
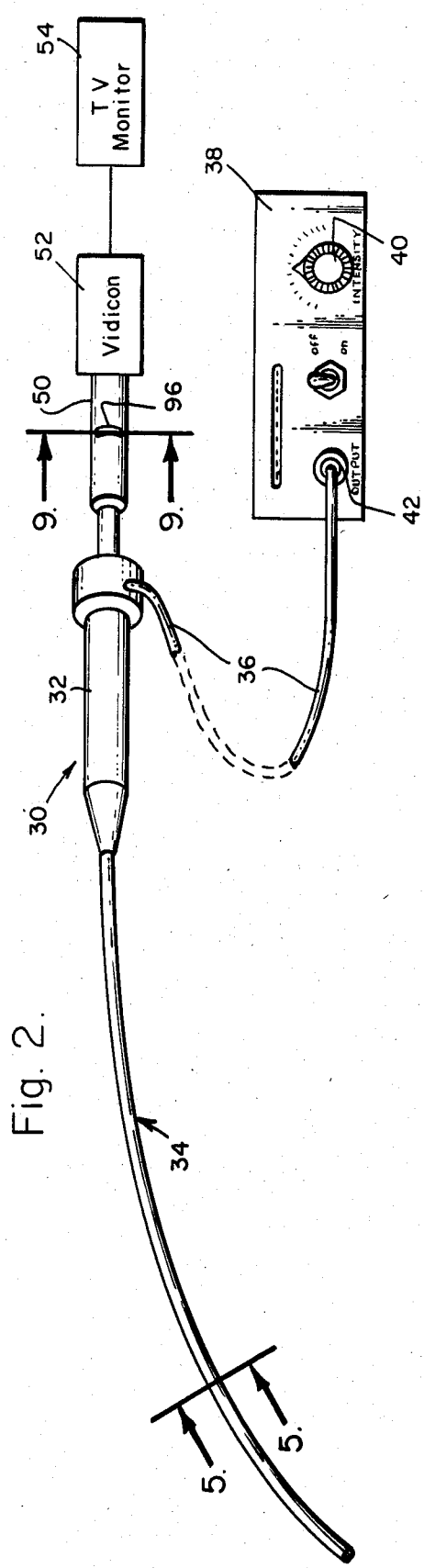
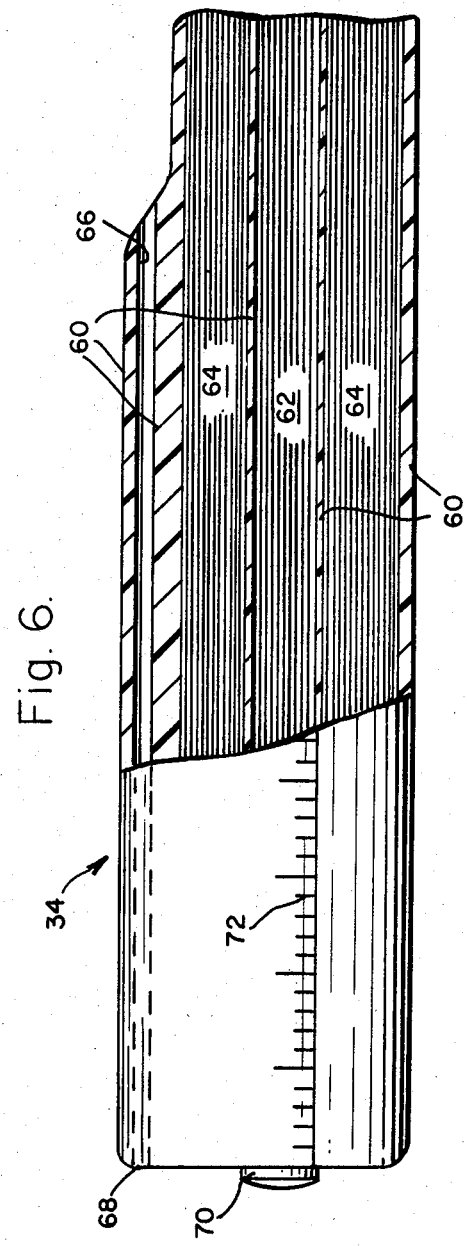

FIBER OPTIC OCULAR ENDOSCOPE

This invention relates to a new improved fiber optic endoscope having particular adaptability for use in examining, diagnosing and treating conditions in the eyes.

The endoscope as a tool became particularly viable with the introduction of fiber optics as a means of bending light. In practice the endoscope comprises a bundle of fiber optics connected to a light source at one end for illuminating an area under investigation. A second bundle of fiber optics coaxial with the first bundle usually contains a lens and/or focusing device for viewing the area under illumination and in which the fiber optics convey the light from the scene under illumination to a remote location where the scene is viewed, usually through a microscope or viewing device having suitable amplification and magnification.

Initially devices of this type were used to investigate and inspect machinery having surfaces and depressions that were not easily viewable such as cylinder walls, turbine blades, bearings, valve seats and the like that could not normally be viewed and/or inspected without completely disassembling the machinery.

As the art developed and the field of fiber optics became more refined, the endoscope probes became smaller and smaller and ultimately these devices found their way into the hands of doctors and surgeons who found them useful for investigating interior portions of the body such as veins and arteries, just to name a few.

For example, a review of U.S. Pat. No. 3,941,121 entitled "Focusing Fiber Optic Needle Endoscope" discloses an improved endoscope having a probe of approximately 18 gauge that has wide applicability in the medical field for treating patients. The disclosed device illustrates how fiber optics, cutting means and focusing controls are located in an endoscope probe having approximately an 18 gauge diameter.

A review of U.S. Pat. No. 3,856,000 entitled "Endoscope" discloses how the endoscope probe may be fitted with a prism that is fully controllable by the operator and allows a scene to be viewed not only in the front but on each side as the prism is rotated.

U.S. Pat. No. 4,211,229 entitled "Laser Endoscope" illustrates still another improvement on the basic endoscope which includes a telescope and a laser lens system for not only inspecting areas under illumination but also treating these areas with coherent light signals under control of the operator. The specific instrument may be a cystoscope, a bronochoscope, a laparascope or a rectoscope, depending on the specific therapy being applied. The concept of viewing and treating from a single instrument was a big step forward in the endoscope art.

Other patents relating to endoscopes include U.S. Pat. No. 3,880,148 entitled "Endoscope" which discloses rotating optical elements located in the sheath under control of the operator for allowing vision over a wide angle. In addition, U.S. Pat. No. 4,061,135 entitled "Binocular Endoscope" discloses still another adaptation of adopting the basic endoscope for binocular vision by having a plurality of channels fed to separate eye pieces.

In the present invention there is described an endoscope that has particular adaptability for use by the eye surgeon in treating, examining and diagnosing problems associated with the eye.

In the art as practiced today, examinations of the eye are typically made by first dilating the eye and assuming the patient has a clear cornea and lens, the doctor places an external lens on the outside and by suitable optics he is capable of looking into the eyeball in order to investigate and view conditions that need treatment.

Within the field of view of the optics, the doctor is capable of inserting irrigation instruments and cutting instruments that can be used to cut fibers and blood vessels, and at the same time provide irrigation, all within the framework of the optical system.

Unfortunately the field of view is limited depending on the optics used and also depending on the condition of the patient's iris and lens.

It is quite clear that if the iris is cloudy or the lens imperfect that it is then impossible for the doctor to view the interior of the eyeball, thereby making treatment extremely difficult or even impossible in certain conditions. In any event, treatment of those areas out of the field of view of the optics makes it impossible for any surgery or treatment. For example, areas on the underneath side of the iris and towards the pupil cannot be treated for the simple reason they can't be seen from the outside.

In the present invention there is described an endoscope that is capable of being inserted into the eyeball and in a manner that is capable of being controlled by the doctor which now allows him to view the internal portions of the eye from inside the eye and in a manner that has heretofore been impossible.

Utilizing the endoscope described in this invention, it is now possible to view areas beneath the iris and on the side of the iris that were otherwise impossible to view or reach before. By attaching a laser to the endoscope it is now possible to treat areas that could not even be reached much less viewed by the external lenses used in the prior art. For example, one of the leading causes of glaucoma is a disease called rubeosis which leads to an accumulation of fluid that cannot be relieved and hence builds up a pressure within the eye. It is now possible to treat these areas by means of the endoscope having laser capabilities as described herein.

The concept is revolutionary in that television monitors are attached to the output of the endoscope and have produced video pictures that show the underside of the iris viewed by the endoscope. The endoscope has been able to take pictures looking out through the pupil of the patient from the inside and view what the patient would normally see. These television images distinctly show cabinets in the room within the field of view of the patient as seen from inside of the patient and as viewed by the endoscope looking out the patient's pupil.

A recent examination procedure performed by the inventors illustrates the removal of a cataract in a patient's eyeball. The scene is viewed from inside the eye showing the removal of the cataract. The ability to work within close tolerances with the endoscope allows the instrument to move within a millimeter of the retina.

With the prior art devices looking from the outside the doctor had to judge his depth of field and be very careful of touching the retina or any other area that could cause irreversible damage to the sight of the patient being examined or operated on.

The endoscope having these capabilities comprises a first bundle of fiber optics connected at one end to a light source for illuminating areas under investigation. A second bundle of fiber optics coaxial with said first bundle terminates at one end at a lens that is used to view the area being illuminated by the first bundle. The second end also terminates at a lens which is aligned with a vidicon camera that feeds a TV monitor screen. In the broadest sense no focusing controls are necessary since the vidicon camera is focused on the output lens of the second bundle of fiber optics and hence the TV monitor shows everything within the field of view of the viewing lens that is illuminated by the first bundle of fiber optics.

Also included within the endoscope is a conduit located coaxial with the first and second bundle which is used primarily for treating those areas under investigation. In the preferred embodiment the conduit is filled with fiber optics that are connected at one end to a coherent light source such as a laser which is under the control of the doctor and which is used for treating those areas under investigation. The conduit may also be used for accepting cutting devices, for taking sample necessary for biopsy measurements as determined by the physician.

The endoscope probe is completely encompassed by a sheath that is made capable of assuming and holding any desired shape and which has an elliptical cross-section.

The elliptical cross-section was found to be a necessary requirement for the sheath probe of the endoscope since this preferred shape not only allows easy insertion of the probe within the eyeball, but also it was discovered that the incision made by the surgeon in the eyeball also formed an elliptical shape thereby allowing the elliptical shape of the probe to very closely conform to the incision shape which enhances the insertion of the instrument within the eyeball and also minimizes loss of liquids and risk of infection.

Maneuvering the endoscope probe is a very delicate and precise maneuver that is continuously monitored by the physician on the television monitor. The specific shape of the sheath is usually preformed by the physician as determined by the treatment being performed in the areas to be investigated.

In the preferred embodiment the external sheath contains a plurality of scale marks in order to assist the doctor as to the distance of penetration of the probe within the eyeball.

In one embodiment the sheath is typically constructed of plastic and made semi-rigid by utilizing silver alloy strands embedded in the plastic in order to give the probe the semi-rigid malleable form that is needed in directing the probe.

In the broadest sense it is required that the probe be malleable and made semi-rigid in order for the sheath to be capable of holding the preferred shape as determined by the physician.

There are different embodiments used to create a malleable semi-rigid endoscope probe. The preferred probe presently being used comprises a pure plastic sheath having an elliptical or oval cross-section which encompasses the first bundle of fiber optics used to illuminate the scene and a coaxial second bundle of fiber optics for viewing the scene under investigation.

In the preferred embodiment an additional conduit is located coaxial with the first and second bundle and is located within a portion of the sheath and preferably at a point of maximum curvature. In this embodiment the sheath is made of pure plastic material and the rigidity needed to preform the shape of the endoscope probe is obtained by a separate malleable probe which is inserted within the defined conduit. The probe, being malleable and capable of assuming any desired shape, is inserted within the defined conduit and then formed by the physician to any desired shape depending on the area of the eye that will be examined and treated. The endoscope probe by definition will conform to the shape of the malleable probe, thereby giving the physician absolute control of where the probe is and its movement through the eyeball.

The malleable probe may be hollow or filled with fiber optics and connected at the opposite end to a laser source for treating those selected portions under investigation.

Further objects and advantages of the present invention will be made more apparent by referring now to the accompanying drawings wherein:

FIG. 1 illustrates the prior art techniques of making a fundoscopic examination of the eye;

FIG. 2 illustrates an endoscope costructed according to the teachings of this invention;

FIG. 3 illustrates a filter flywheel for changing the color illumination of the light source;

FIG. 4 illustrates a second embodiment for inserting filters in the light source;

FIG. 5 is a cross-section taken along lines 5—5 of FIG. 2;

FIG. 6 is a longitudinal cross-section taken of the flexible probe of FIG. 2;

FIG. 10 illustrates the use of an ocular endoscope in treating, diagnosing and examining the eye.

Figure 9:
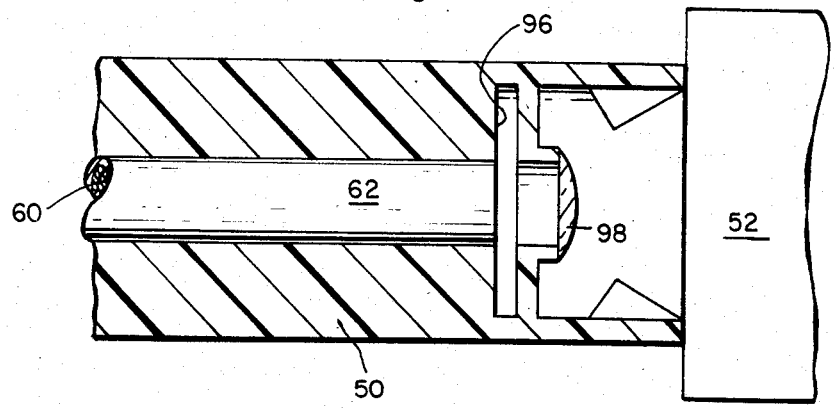
FIG. 9 illustrates a cross-section taken along lines 9—9 of FIG. 2.

Referring now to FIG. 1, there is shown an example of how present-day opthamologists investigate and treat problems within the eye.

The doctor prepares the patient by having the pupils dilated and then places the head of the patient in a suitable support containing a lens 10 that is adapted to fit over the eye 12 as shown in FIG. 1. With the eye properly dilated and assuming the patient has a clear cornea and lens, it is possible for the doctor to look within the eyeball and look into the vitreous body 14 which forms the inside of the eye 12.

In this configuration it is possible for the doctor to introduce an instrument, probably an irrigation/aspiration type device having a cutting capability, that allows him to cut fibers and remove pieces by means of the aspiration device for investigation and possible biopsy examinations. These devices are typically in the neighborhood of one to two millimeters in diameter and represent the surgical instruments presently in use today.

Before the advent of the present invention there were no techniques for looking in the eye except to place the big lens 10 on top of the eye and visually examine the inside of the vitreous body 14.

The geometry of the eye is such that the area of investigation is limited in that it is impossible to see those areas that are in a lateral position with respect to the lens 16 such as the ciliary part of the retina 18 or the ora sarrata 20, which portions are out of the field of view and hence not viewable through the lens 10.

There have been experiments utilizing mirrors that increase the angle within the lens, however, there is a limit to just how far it can be viewed from outside of the eye.

With the advent of the endoscope as described in the present invention, it is now possible to insert the endoscope within the vitreous body 14, thereby allowing the physician to see areas that were otherwise not viewable and in addition to now allow him to view the underside of the iris 22 and thereby allow the doctor to do surgery that was heretofore impossible. By attaching a laser to the endoscope it is now possible to treat areas that were otherwise untreatable and which now gives hope that one of the leading causes of glaucoma can be treated by relieving pressure as fluid builds up in the area of the canal of schlemm 24.

One of the major problems affecting the surgeon in using the lens technique of FIG. 1 is that of always determining the depth of field when using either the cutting tools or the irrigation or aspiration devices within the vitreous body 14. For example, it is quite important when operating within the eye that the retina 15 not be touched and hence the skill of the surgeon in judging his depth of field when operating within the vitreous body 14 is extremely critical and also very dangerous for the patient.

Referring now to FIG. 2, there is shown an endoscope constructed according to the teachings of this invention which makes it primarily adaptable for insertion into the eye in order to view the internal aspects of the eye from inside rather than from outside as is now the current practice.

FIG. 2 illustrates a fiber optic endoscope 30 sufficiently small in size to permit entry into the eye through an incision varying in size from 250 microns to approximately 3 millimeters. The endoscope 30 provides for visualization in a range of focus from one millimeter to infinity and also provides for fiber optic delivery of illumination and a high intensity conduit for conduction of high intensity light for therapeutic applications.

The endoscope 30 comprises a handle portion 32 connected at one end to a flexible scope 34 that is approximately 1000 millimeters long. The flexible scope is more fully described in FIGS. 5 and 6 and contains conduits for holding a bundle of coaxial fiber optics connected to a light source, and a bundle of coaxial fiber optics connected to a lens for viewing areas under illumination. The flexible scope 34 is preferably covered by a plastic sheath having an elliptical cross-section that is more fully illustrated in FIG. 5.

The bundle of fiber optics located in flexible scope 34 are contained within the body 32 and those fiber optics adapted to be connected to a light source pass through a flexible conduit of fiber optics 36 to a light source 38.

The external light source 38 is of conventional construction and contains a light intensity control 40 and a light output jack 42 to which the flexible fiber optic sheath 36 is connected. The output jack 42 is adapted to receive either a filter wheel 44 as illustrated in FIG. 3 or a filter paddle 46 as illustrated in FIG. 4 which thereby allows the operator to control the color of the light source being fed through the fiber optics of conduit 36 and flexible scope 34.

The bundle of fiber optics located in the flexible scope 34 and used for viewing the area under illumination is fed to a separate housing 50 connected to the body 32 and terminates in a lens 98 as is more fully illustrated in connection with FIG. 9. A vidicon camera 52 is adapted to be focused on the lens arrangement located in body 40 while the output of the vidicon is fed to a TV monitor 54 thereby allowing the operator of the endoscope 30 to view all areas under illumination as the flexible scope 34 is inserted and moved within the eye.

The light source 38 provides for low intensity illumination and when used with the various color filters as shown by either the filter wheel 44 illustrated in FIG. 3 or the filter paddle 46 illustrated in FIG. 4 allows the operator to control the changing of the light from the source to provide different wave lengths that allow intra-ocular fluorescein examinations that can be made green or red free as required by the physician. The light intensity control 40 located on the light source 38 also allows the operator to control the light source for changing color temperature and/or intensity associated with monitoring or making video recordings from the TV monitor 54.

In the preferred embodiment a separate dedicated conduit or channel is provided to allow photo radiation to the tip of the endoscope flexible probe 34 for photo radiation treatment of ocular tissues or those substances situated in ocular components. This is more fully illustrated in connection with FIGS. 6, 7, 8 and 9.

The endoscope 30 allows viewing of the interior structure of the eye through a small pars plana incision thereby allowing the opthamologist a better visualization of the interior of the eye and in turn provides a simultaneous route for treatment of intra-ocular diseases. The endoscope also provides a delivery system to conduct delicate intraocular surgery utilizing xenon light, argon laser light, yag laser or laser light of variable wave lengths as will be described in connection with FIG. 9.

One of the main problems associated with ocular endoscopes was the shape of the flexible scope 34 when inserted within the incision made in the eye. It was also discovered that it was necessary for the flexible scope 34 to be capable of assuming a semi-rigid position in order to allow the opthamologist to guide the tip of the flexible scope into any given desired position of the eye. Consistent with these requirements is the fact that the dimension of the diameter of the flexible scope had to be as small as possible consistent with the needs of illuminating, viewing and treating of conditions in the eye.

Referring now to FIG. 5, there is shown a cross-section of the flexible scope 34 illustrated in FIG. 2 taken along lines 5—5. The flexible scope 34 has an elliptical shape which in the preferred embodiment has a long dimension of approximately 1.8 millimeters or less and in the short dimension approximately 0.8 millimeters or less. The elliptical shape was found necessary to ensure ease of insertion of the end of the flexible scope 34 into the incision made in the eye since the incision itself it was discovered also has an elliptical shape once the cut is made. The elliptical cross-sectional shape of the flexible scope 34 has the unobvious advantage of not only being easy to insert but also matches the shape of the incision, thereby reducing the chance of infection since the incision adheres to the surface of the flexible scope.

A plastic sheath 60 completely encompasses the flexible scope 34 and contains within its confines a first bundle of fiber optics 62 that is used for observing and viewing items under investigation. The opposite end of the fiber optic bundle 62 is channeled through the housing 32 as shown in FIG. 2 and terminates in housing 50 in a lens 98 more fully illustrated in FIG. 9. The vidicon camera 52 illustrated in FIG. 2 is focused on the terminating lens to allow the TV monitor 54 to completely monitor all acts being viewed by the fiber optic bundle 62 shown in FIGS. 5 and 6.

Also located within the sheath 60 is a second plurality of fiber optics generally identified as 64 and which are connected to the light source 38 as illustrated in FIG. 2. In operation, light generated in the light source 38 is fed through flexible conduit 36 through the body 32 and through the flexible scope 34 and terminate in fiber optic bundle 64 for providing illumination against those areas selected by the opthamologist. The intensity of the light and the filtering arrangement is under complete control of the opthamologist as shown by the controls on the light source 38 illustrated in FIG. 2.

In the preferred embodiment illustrated in FIG. 5, there is illustrated a separate conduit 66 located in a portion of the sheath 60 that is located in an area of maximum curvature of the sheath. The conduit 66 is preferably used as a laser delivery port by inserting additional fiber optics within the port and connecting these fiber optics to a suitable laser light source which the opthamologist can now use to treat those areas under observation as the flexible scope 34 is maneuvered within the eye.

There are many modifications of the flexible scope 34, however, some modifications have been more successful than others.

In developing the preferred embodiment as illustrated in FIGS. 5 and 6, it was soon realized that a circular cross-section contained a high risk of infection and that manipulating the circular flexible scope under the hands of the opthamologist had the effect of damaging the fiber optics located within the external sheath 60.

In the broadest sense it is necessary that the flexible scope 34 be capable of assuming a preferred semi-rigid shape and thereby eliminate the need of the opthamologist to rotate the flexible scope and damage the internal fiber optics. Consistent with these requirements is the fact that the smallest diameter of the flexible scope 34 preferably should be as small as possible and preferably of the order of no more than 2 millimeters.

Making the flexible scope 34 semi-rigid and malleable has presented a problem and is the subject matter of continuous investigation. Obvious suggestions have included the use of different plastic formulations for the sheath 60 which would allow the sheath to hold the flexible scope 34 in a preferred position as preset by the opthamologist.

Placing silver strands located wholly within the plastic sheath 60 have also provided a flexible scope with the ability to retain its preset shape.

Changing the structure of the sheath 60 and using silver strands have produced a malleable semi-rigid flexible scope 34, however, they have not been satisfactory. The cross-sectional diameter of the flexible scope 34 has increased, thereby creating a larger diameter flexible scope than that illustrated as the preferred embodiment illustrated in FIGS. 5, 6 and 7.

Referring now to FIG. 6, there is shown a longitudinal cross-section of the flexible scope 34 illustrated in FIG. 2.

The longitudinal cross-section illustrated in FIG. 6 more fully illustrates a section of the flexible scope 34. The sheath 60 completely encompasses the viewing bundle of fiber optics 62 which are coaxial with the illuminating bundles of fiber optics 64.

The terminating end 68 of the flexible scope 34 is common with respect to the illuminating bundle of fiber optics 64 and the viewing bundle of fiber optics 62. A suitable lens 70 is located in the end portion of the viewing bundle of fiber optics 62.

Located within the outer sheath 60 and preferably at a point of maximum curvature of the sheath is the port 66 which extends from the end 68 for a length of approximately 30 millimeters along the length of the flexible scope 34 from the end 68. The port 66 is an access port that is capable of being used for a plurality of different functions.

In the preferred embodiment it is most important that the opthamologist have complete control of the movement of the end portion of the flexible scope 34 and that the flexible scope be semi-rigid and malleable in order to assume any given shape imparted to it by the user. Consistent with this requirement is the fact that the cross-sectional area should be maintained as an ellipse as shown in FIG. 5 and, further, that the smallest dimension be as small as practicable and preferably of the order of 2 millimeters.

FIG. 6 shows a cutaway portion of the end 68 of the flexible scope 34 which more fully illustrates metric scale markigs 72 located on the periphery of the flexible scope 34 in the portion of the end 68. These markings are located on the outside of the sheath 60 and help the opthamologist in determining the depth of penetration of the tip of the endoscope into the eye.

A solid silver wire or alloy of silver that is semi-rigid and malleable could also be inserted into port 66 and thereby allow the doctor control over the shape of the flexible probe 56.

Figure 7:
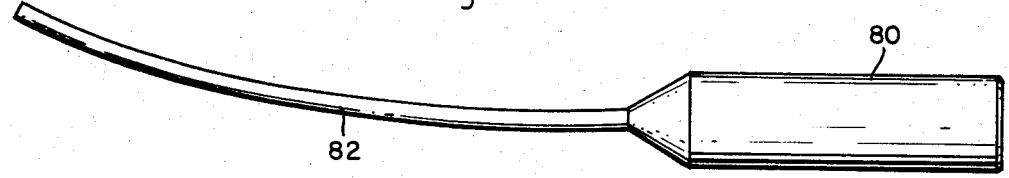
FIG. 7 illustrates a semi-rigid probe for controlling the shape of a flexible endoscope.

Referring now to FIG. 7, there is shown a handle 80 attached at one end to a malleable semi-rigid probe 82 that is capable of being formed in any given shape as determined by the opthamologist. The diameter of the probe 82 is sized to fit within the conduit 66 illustrated in FIG. 6.

In this fashion the doctor by holding handle 80 and inserting probe 82 ito the conduit 66 now has control over the end portion of the flexible scope 34 and at the same time the end portion of the flexible scope will conform to the desired shape imparted on probe 82.

Figure 8:
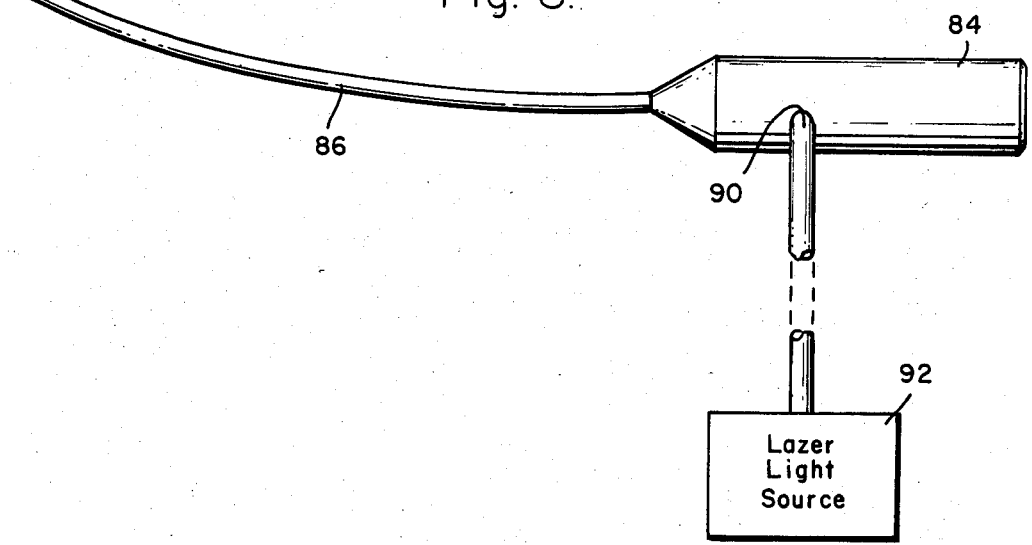
FIG. 8 illustrates a second embodiment of the probe illustrated in FIG. 7.

Referring now to FIG. 8, there is shown a second embodiment comprising handle 84 and the probe 86 in which the probe 86 is hollow and contains a bundle of fiber optics that extend from inside the probe and exit from the handle 84 at a port 90. The bundle of fiber optics from port 90 is connected to a laser light source 92 which is under the control of the opthamologist and can be used for treating those areas in the eye that are being illuminated and observed.

Referring now to FIG. 9, there is shown a cross-section taken alonng lines 9—9 of the figure illustrated in FIG. 2.

The cross-sectional area illustrated in FIG. 9 of light chamber 50 illustrates the termination of the viewing bundle of fiber optics 60 which terminate at a slot 96. A lens 98 is focused on the terminating end portion of the fiber optics 60 and all scenes under illumination and viewed by fiber optics 60 will be fixed focused upon the lens 98. The vidicon camera 52 is focused on the lens 98 and hence will record all scenes being viewed by the opposite end of the fiber optics 60, which scenes will be displayed upon the TV monitor 54 illustrated in FIG. 2.

The slot 96 is adapted to receive either a circular filter wheel 44 of the type illustrated in FIG. 3 or a filter paddle 46 as illustrated in FIG. 4. The specific filters used will be under the control of the opthamologist while using the endoscope for either treating, diagnosing or investigating problems within the eye.

A review of the prior art techniques as shown in FIG. 1 will show that present methods necessary to operate under intra-ocular conditions require a clear cornea, adequate anterior chamber clarity, moderate pupil area openings, relatively clear lens or absence of significant lens opacities. Frequently corneal injuries, corneal opacities or scars, for example, anterior chamber hemmorage or opacities, dense cataracts or intra-ocular membranes obstruct adequate view of intra-ocular structures thereby preventing the optometrist from getting a clear view from the outside lens.

By utilizing the ocular endoscope as illustrated in FIG. 2, there is provided an excellent internal viewing device capable of providing adequate viewing even if corneal scars, anterior hemmorage, dense cataracts or other opacities are present. In addition, treatment modalities that require similar clear visual access could be performed such as laser or xenon light treatment through the endoscope by utilizing the embodiments illustrated in connection with FIG. 9.

Referring now to FIG. 10 there is shown a cross-sectional view of an eye 12 which illustrates how the endoscope 30 can be used to treat and diagnose and investigate problems located within the eye itself.

FIG. 10 illustrates the vitrectomy of intravitreal stands and tension detachment. The endoscope 30 is inserted within the eyeball through an incision preferably made near the tendon of lateral rectus muscle 100 and is inserted within the vitreous body 102 in the eyeball until the detached strands 104 are detected. The vitrector 106 is preferably inserted through an incision on the opposite end of the eye 12 under the complete guidance of the endoscope 30 which has the ability of illuminating and viewing selected areas. In this environment the doctor can position the vitrector 106 while under direct view through the endoscope and then cut, aspirate and irrigate as required.

This procedure of inserting the endoscope 30 within the eye eliminates the problem of the depth of field of using outside lenses since the vitrector is under the direct view and control at all times through the viewing end of the endoscope 30.

We claim:

1. An ocular endoscope comprising:
   a first bundle of fiber optics adapted to be connected to a light source at one end for conducting and projecting light to selected areas at the other end,
   a second bundle of fiber optics coaxial with said first bundle and adapted to be connected to a display device at one end and a lens at the other end for viewing said areas illuminated by said first bundle, and
   a semi-rigid malleable flexible sheath encompassing said first bundle and said second bundle, said sheath, said first bundle and said second bundle of fiber optics having a cross-section approximating that of an ellipse whereby insertion of the probe is facilitated by conforming to the shape of the incision and risk of infection is minimized.

2. An ocular endoscope comprising:
   a first bundle of fiber optics adapted to be connected to a light source at one end for conducting and projecting light to selected areas at the other end,
   a second bundle of fiber optics coaxial with said first bundle and adapted to be connected to a display device at one end and a lens at the other end for viewing said areas illuminated by said first bundle,
   a conduit located coaxial with said first and second bundle and adapted to receive an external probe, and
   a sheath encompassing said first bundle, said second bundle and said conduit in a flexible arrangement and having an elliptical cross-section.

3. An ocular endoscope according to claim 2 which includes a malleable probe inserted in said conduit whereby the external form and shape of said sheath can be formed to any desired shape.

4. An ocular endoscope according to claim 2 in which said conduit is located in a portion of said sheath.

5. An ocular endoscope according to claim 4 in which said conduit is located at the point of greatest curvature of said sheath.

6. An ocular endoscope according to claim 2 in which said sheath is constructed of plastic.

7. An ocular endoscope comprising:
   a first bundle of fiber optics adapted to be connected to a light source at one end for conducting and projecting light to selected areas at the other end,
   a second bundle of fiber optics coaxial with said first bundle and adapted to be connected to a display device at one end and a lens at the other end for viewing said areas illuminated by said first bundle,
   a conduit located coaxial with said first and second bundle,
   a sheath encompassing said first bundle, said second bundle and said conduit in a flexible arrangement, and
   a semi-rigid malleable probe capable of assuming and holding any desired shape and adapted to be inserted in said conduit whereby said sheath is made to conform to the shape of said probe.

8. An ocular endoscope according to claim 7 in which said sheath holding said first bundle, said second bundle and said conduit has an elliptical cross-section.

9. An ocular endoscope according to claim 7 in which said conduit is located in said sheath.

10. An ocular endoscope according to claim 9 in which said conduit is located in a portion of said sheath having the greatest curvature.

11. An ocular endoscope according to claim 7 in which said probe is hollow and adapted to receive diagnostic testing and treating devices.

12. An ocular endoscope according to claim 11 in which said hollow probe contains a bundle of fiber optics connected to a laser source for treating said illuminated areas.

13. An ocular endoscope according to claim 7 in which said second bundle of fiber optics terminates at a lens at the display device end.

14. An ocular endoscope according to claim 12 in which said display device includes a television vidicon camera focused on said lens and feeding a video signal to a television monitor for viewing said area illuminated by said first bundle.

15. An ocular endoscope according to claims 1, 2 or 7 in which said display device is a television monitor.

* * * * *